US006491939B2

(12) United States Patent
Kubek

(10) Patent No.: US 6,491,939 B2
(45) Date of Patent: Dec. 10, 2002

(54) PHARMACOTHERAPEUTIC PROCESS AND COMPOSITION FOR CENTRAL NERVOUS SYSTEM DISORDERS

(75) Inventor: Michael J. Kubek, Indianapolis, IN (US)

(73) Assignee: Advanced Research and Technology Institute, Inc., Indianapolis, IN (US)

(*) Notice: Subject to any disclaimer, the term of this patent is extended or adjusted under 35 U.S.C. 154(b) by 0 days.

(21) Appl. No.: 09/897,179

(22) Filed: Jul. 2, 2001

(65) Prior Publication Data

US 2002/0004062 A1 Jan. 10, 2002

Related U.S. Application Data

(62) Division of application No. 09/242,776, filed as application No. PCT/US97/15184 on Aug. 28, 1997, now Pat. No. 6,303,134.
(60) Provisional application No. 60/025,171, filed on Aug. 29, 1996.

(51) Int. Cl.[7] .............................. A61F 2/00; A61K 9/48; A61K 9/14; A61K 9/16; A61K 9/50

(52) U.S. Cl. ........................ 424/423; 424/422; 424/451; 424/484; 424/489; 424/490; 424/497

(58) Field of Search ................................. 424/423, 422, 424/451, 484, 489, 490, 497

(56) References Cited

U.S. PATENT DOCUMENTS

| 4,849,228 A | | 7/1989 | Yamamoto et al. |
| 5,171,812 A | * | 12/1992 | Domb ...................... 526/318.2 |
| 5,360,610 A | | 11/1994 | Tice et al. |
| 5,487,739 A | | 1/1996 | Aebischer et al. |
| 5,652,220 A | * | 7/1997 | Heya et al. .................. 514/18 |

FOREIGN PATENT DOCUMENTS

EP      0256726 B1  *  2/1988

OTHER PUBLICATIONS

Saunier et al., "Cyclic AMP regulation of Gs protein", The Journal of Biological Chemistry, vol. 265, No. 32, Nov. 15, pp. 19942–19946, 1990.*
Eyal Ron et al., "Controlled release of polypeptides from polyanhydrides", Proc. Nat'l Acad. Sci. USA, vol. 90, pp. 4176–4180 (May 1993).*
George A. Mason et al. "Thyrotropin–Releasing Hormone", pp. 1–11, 2000.*
"P8/21 Thyrotropin Releasing Hormone (TRH) in Ultra Low Doses Decreases Severity of Seizures in Rats", N.E. Chepournova et al., Neuropeptides 26 (Supp. 1):52 (1994).
"Seizure suppression in kindling epilepsy by intracerebral implants of GABA–but not by noradrenaline–releasing polymer matrices", Merab Kokaia et al, E P Brain Res (1994), 100:385–394.
"Interstitial Chemotherapy of the 9L Gliosarcoma: Controlled Release Polymers for Drug Delivery in the Brain", Rafael J. Tamargo et al., Cancer Res. 53:329–33 (1993).
"Anticonvulsant Effect of DN–1417, a Derivative of Thyrotropin–Releasing Hormone, and Liposome–Entrapped DN–1417, on Amygdaloid–Kindled Rats", Norio Mori et al., Epilepsia, 33(6):994–1000 (1992).

(List continued on next page.)

Primary Examiner—Thurman K. Page
Assistant Examiner—Rachel M. Bennett
(74) Attorney, Agent, or Firm—Leydig Voit & Mayer, Ltd.

(57) ABSTRACT

Methods and compositions are disclosed for providing prolonged-release of therapeutic agents by way of in situ stereotaxic implantation in specific loci, including pathways, to treat known disorders. One or more microstructures comprising therapeutic agents and pharmaceutically acceptable carriers are implanted, for example, through a cannula. The microstructures are of a sufficient size and shape to prevent dispersion from the implant site.

14 Claims, 8 Drawing Sheets

OTHER PUBLICATIONS

"Controlled release of polypeptides from polyanhydrides", Eyal Ron et al., Proc. Nat'l. Acad. Sci. USA, vol. 90, pp. 4176–4180 (May 1993).

"Drug Delivery to the Brain Using Polymers", Abraham Domb et al., Critical Reviews in Therapeutic Drug Carrier Systems, 8(1):1–17 (1991).

"The intracerebral distribution of BCNU delivered by surgically implanted biodegradable polymers", Stuart A. Grossman, M.D., et al., J Neurosurg 76:640–647 (1992).

"$G_i$ Down–regulation as a Mechanism for Heterologous Desensitization in Adipocytes", Allan Green et al., The Journal of Biological Chemistry, vol. 267, No. 5, pp. 3223–3229 (1992).

"Agonist regulation of cellular G protein levels and distribution: mechanisms and functional implications", Graeme Milligan, TIPS, vol. 14, pp. 413–418, (Nov. 1993).

"Thyrotropin–Releasing Hormone–Induced Subcellular Redistribution and Down–regulation of $G_{11\alpha}$: Analysis of Agonist Regulation of Coexpressed $G_{11\alpha}$ Species Variants", Molecular Pharmacology, 49:646–655 (1996).

Kim et al., "The Long Isoform of Rat Throtropin–releasing Hormone Receptor Down–regulates Gq, Journal Biology Chemistry" Chem. Abstr., vol. 269(31), pp. 19933–40 (1994).

* cited by examiner

PHARMACOTHERAPEUTIC PROCESS AND COMPOSITION FOR CENTRAL NERVOUS SYSTEM DISORDERS

CROSS-REFERENCE TO RELATED APPLICATION

This application is a divisional of Ser. No. 09/242,776 filed Feb. 22, 1999, now U.S. Pat. No. 6,303,134, which is a 371 of PCT/0597/15184 filed Aug. 28, 1997 based upon U.S. provisional application No. 60/025,171 filed Aug. 29, 1996, and entitled Novel Pharmacotherapeutic Process and Composition for Central Nervous System Disorders.

BACKGROUND OF THE INVENTION

The present invention relates generally to methods and compositions for locally inhibiting release of selected endogenous compounds, as might be particularly useful for inhibiting glutamate and aspartate release in central nervous system loci.

Therapeutic treatment of various central nervous system disorders has been difficult to achieve because of the failure to provide sustained drug delivery. For example, Thyrotropin-releasing hormone (TRH), an endogenous central nervous system tripeptide, as well as TRH analogs, have been shown to have effective but transient anticonvulsant effects in a variety of animal seizure models. Nevertheless, therapeutic treatment utilizing TRH has been previously unsuccessful in the treatment of epilepsy. In this regard, patients suffering intractable seizures benefited only briefly from repeated TRH and TRH analog treatment.

In particular, oral and injected delivery of TRH and other neural peptides as therapeutic agents have been inadequate because of poor penetration of the drug to the desired site. Contributing factors to the limited site-specific bioavailability of therapeutic agents in the central nervous system include rapid peripheral metabolism, poor intestinal absorption, insufficient blood brain barrier penetration, inability to use synthetic precursors, and untoward side effects. As a result, delivering the neural peptide systemically by way of general circulation and/or cerebrospinal fluid would undesirably distribute the neural peptide to nonspecific receptor sites, thereby causing untoward side effects both systemically as well as in the central nervous system.

In U.S. Pat. No. 5,360,610, Tice et al. disclose polymeric microspheres, having diameters ranging from 5 to 45 micrometers, as injectable, drug-delivery systems for delivering bioactive agents to sites within the central nervous system. However, the injectable microspheres described by Tice et al. are ill-suited to provide sustained drug delivery to central nervous system loci because the microspheres tend to disperse in extracellular cerebrospinal fluid (CSF) and are subject to nonspecific uptake and delivery to more distant sites in the brain by CSF through the circumventricular organs, glia and neurons themselves. Larger microspheres are also inadequate because of insufficient rate of release of the bioactive agent from the interior of the microsphere to the site to be treated.

Other prior art approaches have involved use of lipophilic analogs of known neuropeptides, or lipophilic organic look-a-like compounds at a high affinity neuropeptide binding site to mimic endogenous neuropeptide activity, in the hope of enhancing drug delivery to promote long-lasting effects. However, these approaches have been ineffective because of widespread distribution of the neuropeptide analog to nontargeted receptor sites resulting in untoward side effects. In addition, other previous attempts have included osmotic minipumps, attachment to liposomes and cerebroventricular infusion. These attempts have also been ineffective because osmotic minipumps need replenishment, can become clogged and are a source of potential cerebral infection. Liposome attachment results in widespread distribution including non-targeted receptor sites resulting in untoward side effects. Cerebroventricular infusion results in a short duration of action and widespread distribution to non-targeted receptor sites leading to side-effects.

From the foregoing, it will be appreciated that there exists a need in the art for site-specific drug delivery to central nervous system loci in which sustained release of the drug is achieved without dispersion of the drug from the original site of implantation which causes nonspecific uptake and delivery to non-targeted receptor sites. It will be appreciated that there also exists a need in the art for site-specific drug delivery in which the release of the drug can be sustained at a relatively constant rate if desired.

SUMMARY OF THE INVENTION

The aforesaid problems are solved, in accordance with the present invention, by compositions and methods for providing prolonged release of therapeutic agents in situ at a specific locus over time. Under the present invention, microstructures are provided to effectively deliver sustained and controllable release of therapeutic agents, such as neuroactive peptides and/or analogs, singly or in combination, by in situ stereotaxic implantation in specific central nervous system loci, including pathways, in order to treat known neurological disorders. The microstructures are most preferably in the shape of microdisks having upper and lower surfaces that are substantially parallel to each other and also having substantially circular perimeters that can be optimally adapted for delivery through a cannula, although the microdisks can include shapes in which the upper and lower surfaces are not substantially parallel, or the perimeters are not circular or even rounded, if desired.

The microstructures include a therapeutic agent which can, for example, serve as an agonist at particular receptor sites in, for example, neurons. The microstructures also include a carrier that is biodegradable at body temperature and is nontoxic. Examples of suitable carriers include polyanhydrides, particularly polymerized oleic acid dimers and sebacic acid polymers. A most preferred carrier is oleic acid dimer identified as poly(FAD-SA). It is to be noted that multiple microstructures can be implanted at a site in accordance with the present invention. In this regard, microstructures containing different drugs which can, for example, have synergistic effects, can be implanted together.

Advantageously, by providing stereotaxic in situ implantation of the long-release microstructures directly into the locus, including pathways, associated with, for example, a neurological disorder, the present invention eliminates barriers to drug delivery. Also, the microstructures of the present invention attenuate the possibility of untoward side effects through the stereotaxic implantation which confines the long-release microstructures to the locus of interest.

By way of example, microstructures of the present invention can be implanted to deliver TRH and/or its analogs to inhibit glutamate and aspartate, which are the primary and most abundant excitatory neurotransmitters used by nerve cells in the brain. By inhibiting glutamate and aspartate release, the microstructures of the present invention can be used to treat a number of neurodegenerative diseases of the central nervous system that are caused by excessive release of these transmitters, including, but not limited to, epilepsy, focal stroke, sclerosis, trauma, ischemia, Alzheimer's dementia and motoneuron disease. Significantly, the sustained release provided by the microstructures of the present invention is essential in providing meaningful inhibition of glutamate and aspartate in order to treat the neurodegenerative disorders. For example, microstructures can be implanted at trauma sites in the spinal cord sustained by accident victims. By delivering TRH and/or TRH analogs to the traumatized spinal cord, the massive release of glutamate that typically accompanies swelling can be precluded thereby preventing excitotoxicity that otherwise kills cells due to the excessive glutamate release.

The present invention will be more fully understood upon reading the following detailed description of the preferred embodiments in conjunction with the accompanying drawings.

DETAILED DESCRIPTION OF THE PREFERRED EMBODIMENTS

The following portion of the specification, taken in conjunction with the drawings, sets forth the preferred embodiments of the present invention. The embodiments of the invention disclosed herein include the best mode contemplated by the inventor for carrying out the invention in a commercial environment although it should be understood that various modifications can be accomplished within the parameters of the present invention.

In accordance with the present invention, microstructures containing a therapeutic agent, such as TRH and/or TRH analogs, and a nontoxic carrier that is biodegradable at body temperature can be used singly or in concert with other microstructures containing the same or other components at specific central nervous system loci. The microstructures of the present invention have significant utility, for example, in the treatment of many neurodegenerative disorders caused by excessive glutamate or aspartate release, such as stroke, epilepsy, ischemia, trauma, sclerosis, Alzheimer's disease and others.

Critically, the microstructures form a size and shape that is sufficiently large to prevent dispersion of the microstructure from one or more selected implant loci while also providing the necessary surface geometry to provide a relatively constant rate of release of the drug by surface erosion to the desired in situ site. The microstructures of the present invention include any shape in which, during erosion, the surface area of the microstructure decreases at a rate less than that of a microsphere, as described in more detail below. In a most preferred embodiment, such non-spherical microstructures may be in the form of microdisks.

Figure 1:
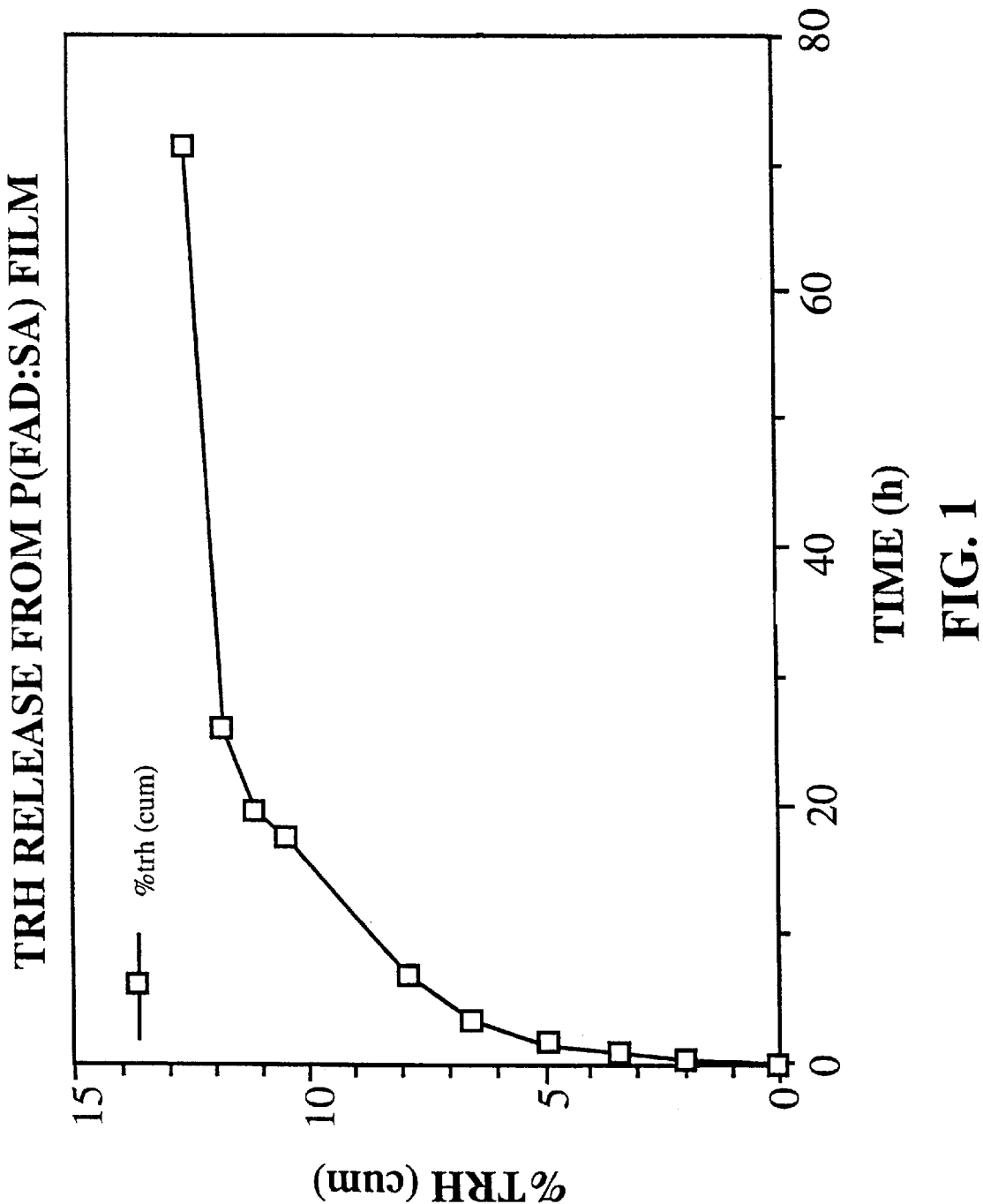
FIG. 1 depicts the rate of TRH release from P(FAD:SA) film.

While the thickness and diameter of the microdisks and other non-spherical microstructures can vary, the microdisks are preferably compatible with commercially available needles having relatively small diameters, for example, 24 to 15 gauge needles. The most ideal size of the microdisks and other non-spherical microstructures will differ depending upon the application but is selected in order to prevent dispersion, as noted above, and must also not be so large as to damage cells during implantation. By way of example, microdisks can have a diameter ranging from approximately 0.3 millimeters to approximately 1.5 millimeters and larger diameters can be inserted through other known stereotaxic methods particularly up to 5 millimeters, and can have an exemplary thickness ranging from about 0.1 millimeters to about 5.0 millimeters, most preferably about 0.2 millimeters. Microstructures having diameters significantly larger than the thickness or having a thickness significantly larger than the diameter are most preferred. Accordingly, the microdisks and other non-spherical microstructures of the present invention can be made larger than the microspheres of the prior art and can therefore avoid the possibility of dispersion in extracellular spinal fluid and they are therefore less susceptible to nonspecific uptake and delivery to more distant sites in the brain by CSF, glia and retrogradely by neurons. In addition, the microdisks and other non-spherical microstructures of the present invention can optimize the rate of drug delivery to the in situ sites. Advantageously, the TRH microdisks of the present invention, for example, provide sustained release as demonstrated by in vitro tests which show that the sustained release can exceed 70 hours, as seen in FIG. 1. This sustained release is important in view of the mechanism for inhibiting neurotransmitter release, as described in more detail herein below.

The TRH, TRH analogs, and/or other active therapeutic agents can comprise from about 1 percent to about 90 percent by weight of the polyanhydride microstructure such as a microdisk. Preferably, the microstructure comprises from about 1 to about 60% of the therapeutic agent in order to optimally control delivery of the drug through the biodegradable matrix, and more preferably, the therapeutic agent comprises from about 1% to about 10% of the microstructure. Also, dose effects can vary depending upon the desired applications, as well. For example, lower doses of TRH and/or TRH analogs can be sufficient to inhibit glutamate release, but in higher doses, the microstructures containing TRH and/or TRH analogs can more effectively eliminate glutamate and aspartate.

It is to be noted that non-spherical microstructures such as microdisks are also advantageously desired over other methods for providing sustained release such as minipumps. For example, drug delivery by microstructures is not susceptible to the increased risk of infection found in the use of minipumps. In addition, minipumps are also relegated to one site, whereas microstructures of the present invention can be advantageously placed in several sites. Further, the microstructures of the present invention have the advantageous capability of sinusoidal delivery. In this regard, the microstructures can be formed with a porous structure, as desired, which can be designed to degrade at differing rates in order to control the release of drug, for example, by selecting differing high and/or low concentration release cycles.

As noted above, the non-spherical microstructures such as microdisks can be multiply implanted but single microstructures can also be implanted if desired. It is most preferred to perform a single implantation at a specific locus in which one or more microstructures are implanted at one time by way of a cannula, and the cannula is then removed with the microstructures then left to biodegrade, without any toxic products, at body temperature of about 37° C. Alternatively, repeated application is also contemplated under the present invention in which the microstructures are applied over time. In this regard, the delivering cannula remains available for microstructures to be implanted at various times and the cannula can be stereotaxically adjusted as desired.

The present invention is not limited by the specific locus selected for drug delivery. For example, TRH can have efficacy in any part of the central nervous system but is more applicably efficacious in regions where the density of TRH receptors is high, particularly, in the amygdala, the hippocampus and other limbic and neocortices, as well as in the spinal cord and the optic retina in the eye.

The carrier facilitates sustained release and eliminates the possibility of burst release in which there is a large loading dose in which for example, 90 percent of the drug is released quickly. In contradistinction, the carriers of the present invention are selected to release a relatively constant amount of active therapeutic agent by erosion from the surface over time. More specifically, over a preselected period of time for sustained release, the rate of change of the surface area of non-spherical microstructures such as microdisks can be designed to change relatively slowly, as opposed to the microspheres of the prior art, which will erode so that the surface area decreases quickly, and are therefore subject to a burst release. This problem of burst release is compounded when the microspheres increase in size. Whereas in an idealized model, the surface area of a sphere will erode at a rate of $8\pi r$ (dr/dt), where r is the radius and (dr/dt) is the time rate of change of r, the surface area of the microstructures of the present invention will decrease with erosion at a rate less than $8\pi r$ (dr/dt), preferably at a rate less than about $3.5\pi l$ (dl/dt), where l is a characteristic size of the microstructure and (dl/dt) is the time rate of change of l. In this regard, the term "characteristic size" refers to a size representative or typical of the microstructure and, in the case of a microsphere, refers to the diameter of the microsphere, while in the case of a microdisk having thickness much less than radius, refers to the diameter of the microdisk.

Referring now to the mechanism of action, the present invention has particular utility in providing an agonist that can modulate release of endogenous compounds, such as neurotransmitters, neuropeptides or hormones, by way of a novel mechanism of desensitizing a heterologous receptor by downregulating G-proteins common to both an agonist, or homologous, receptor and the heterologous receptor that is selected for desensitization. A number of conditions are important in this mechanism for achieving prolonged heterologous receptor desensitization. For example, homologous and heterologous receptors must be highly expressed in the same cell such as a neuron. In addition, the homologous and heterologous receptors must utilize the same G-protein signaling system, for example, $G_i$ or $G_q$. The homologous receptor must be downregulated, that is, effectively reduced, by its transmitter/modulator and agonists. Also, the downregulation of the homologous receptor must be associated with downregulation of its specific G-protein. Critically, sustained receptor exposure with agonist is required for prolonged desensitization to occur.

As an example, the following discussion refers to modulation in the form of inhibition of glutamate release, but it will be appreciated that this discussion is merely exemplary and is not limiting to the present invention. It will be appreciated that the mechanism of the present invention will also function to modulate second messenger systems, including increase in release.

In accordance with one aspect of the present invention, metabotropic glutamate receptors (mGluRs) make up a small portion of the much larger superfamily of G-protein coupled receptors consisting of seven transmembrane spanning regions coupled to second messenger systems, such as adenylyl cyclase/cAMP, phospholipase-C (PLC)/DAG, $IP_3$, by a class of GTPases termed G-proteins. One of ordinary skill in the art will appreciate that G-proteins are heterotrimeric and composed of $\alpha$, $\beta$, and $\gamma$ subunits encoded by a distinct gene. In particular, G-protein $\alpha$ subunits are subdivided into four main classes termed $G_s$, $G_i$, $G_q$, and $G_{12}$. In addition to diversity among $\alpha$-chains, there are also multiple genes encoding at least 4 $\beta$- and at least 6 $\gamma$-subunits. The $\alpha$ subunits appear to be the most important in regulating the signal cascade wherein both fast transmission (ionic) and long-term ($Ca^{++}$-dependent immediate early gene activation) events can be modulated. The $\alpha$ subunits of the $G_q$-like G proteins ($G_{q/11}$) have been observed to play a key role in the regulation of intracellular $Ca^{++}$ levels and in the generation of second messenger systems. Therefore, this effector system is found among the metabotropic glutamate receptors as opposed to the ionotropic receptors (iGluRs) which are the second major category of glutamate receptors. It is to be noted that the iGluRs have been pharmacologically characterized by selective agonists and antagonists into three major classes, NMDA, AMPA, and Kainate. Activation of these receptors results in gating of cations ($Na^+$, $Ca^{++}$) from the extracellular fluid, through a specific ion channel. This ligand-dependent ion gating renders the interior of the target cell less negative, and thus resultant depolarization enhances cell excitability. Several genetic variants of each class of ionotropic receptor have been cloned but none of the ionotropic glutamate receptors are coupled to the G-protein effector pathways.

It is now recognized that a large proportion of the neurotransmitters (glutamate, $GABA_B$, acetylcholine, dopamine, etc.), neuropeptides (TRH, neuropeptide-Y (NPY), cholecystokinin (CCK), neurotensin (NT), etc.), and hormones (glucagon, melatonin, etc.), act through G-protein linked receptors. Presently, eight different mGluR subtypes ($mGluR_{1-8}$) have been cloned and subsequently expressed in various cell lines. The mGluRs have been classified into three groups based on amino acid sequence similarity, agonist/antagonist pharmacology and signal transduction pathways to which they couple. More specifically, group I mGluRs ($mGlu_1$ and $mGlu_5$) stimulate phospholipase-C/DAG, $IP_3$ through $G\alpha_{q/11}$ G proteins. Meanwhile, group II ($mGluR_2$ and $mGluR_3$) and group III ($mGluR_4$ and mGluR$_{6-8}$) are negatively coupled to adenylyl cyclase/cAMP through G$\alpha_{i/o}$G proteins.

The mGluRs are believed to modulate glutamate synaptic transmission via both presynaptic and postsynaptic mechanisms. Inhibition of transmitter release occurs following activation of presynaptic Group II and III mGluRs, most likely through direct G protein-mediated (G$\alpha_{i/o}$) inhibition of Ca$^{++}$ channels, and not through their negative coupling to adenylyl cyclase. In marked contrast, activation of Group I mGluRs enhances glutamate release via a mechanism involving G$\alpha_{q/11}$ G protein-mediated PLC/protein kinase C (a product of DAG activity) inhibition of presynaptic K$^+$ channels.

Postsynaptic Group I mGluRs mediate slow depolarization and an increase in cell firing. This effect appears to be due to a depression of K$^+$ currents directly by G$\alpha_{q/11}$ rather than as a consequence of their coupling to PLC. Postsynaptic Group I mGluRs may also modulate both AMPA and NMDA iGluR-mediated currents indirectly, probably via PKC-mediated phosphorylation of their respective Ca$^{++}$ ion channels.

It is known that activation of Group I receptors (and iGluRs) induces seizures and appears to contribute to excitotoxicity and cell death. In contrast, activation of Group II/III mGluRs reduces glutamate release and produces neuroprotective effects.

From the brief discussion above, it is clear that several ligand initiated events can and are affected by both endogenous transmitter and agonist/antagonist receptor interactions. Recent data have shown that G proteins are critical in the signal transduction pathway and when downregulated can affect activity of both the homologous and a heterologous receptor that utilizes the same G protein signaling cascade. As noted above, of all the glutamate receptors, only mGluRs utilize G protein coupling. Moreover, of the three mGluR subgroups, only Group I mGluRs (mGlu$_1$ and mGlu$_5$) use G$\alpha_{q/11}$ for signal transduction. Importantly, it is well recognized that G$\alpha_{q/11}$ G proteins couple the TRH receptor (TRHr) to PLC for cell signaling. The TRHr is known to be significantly downregulated both by sustained exposure to ligand and following seizures in neurons that co-localize glutamate and TRH as well as their receptors.

Homologous receptor downregulation is essential for G protein downregulation. In this regard, it has been previously demonstrated that sustained exposure (16 hr.) of TRH to the cloned TRHr results in substantial subcellular redistribution and marked dose-dependent downregulation of G$\alpha_{q/11}$ G proteins without affecting cellular levels of the $\alpha$ subunits of G$_s$, G$_{i1-3}$, or G$_o$. Group I mGluRs are the only glutamate receptors that require the G$\alpha_{q/11}$ subunit to affect presynaptic glutamate release and postsynaptic ion channel effects (see above), and sustained TRH exposure to its receptor results in relocation and substantial (20–70%) reduction of G$\alpha_{q/11}$ G proteins. Therefore, the prolonged exposure of the TRHr to ligand, as from the TRH-polyanhydride microstructure carrier in accordance with the present invention, heterologously modulates (uncouples) G$\alpha_{q/11}$ from the Group I mGluR in those cells that express both the TRHr and Group I mGluRs resulting in prolonged Group I desensitization to pre- and postsynaptic glutamate stimulatory effects and potentiation of glutamate-induced Group II/III inhibitory effects.

This mechanism can account, in large part, for TRH effects observed on inhibition of glutamate release and suppression of neuronal Ca$^{++}$ uptake. This novel mechanism of prolonged desensitization of Group I mGluRs by sustained TRH release in situ could account for the enhanced and prolonged duration of antiepileptogenic and anticonvulsant effects of TRH in the kindling model of temporal lobe epilepsy. This effect would not be limited to seizures, and its related cell damage, but could include modulation of other proposed excitotoxic effects of excessive glutamate release as well, including neurodegeneration associated with neurotrauma, stroke, ischemia and Alzheimer's dementia. Thus, it is clear that heterologous desensitization by TRH could result with other G protein receptors that utilize G$\alpha_{q/11}$ coupled signaling cascades. However, receptors that use G$\alpha_{q/11}$ coupling are remarkably restricted and include only the M1 acetylcholine receptor and a limited number of neuropeptides and hormones such as neurotensin, vasopressin and bradykinin.

In order to promote a further understanding and appreciation of the present invention and its attendant advantages, the following specific examples are provided. It will be understood that these examples are illustrative and not limiting in nature.

EXAMPLE 1

Materials and Methods

TRH microstructures were produced from an anhydride copolymer of fatty acid dimer (FAD) and sebacic acid (SA) in a 50:50 ratio, Poly (FAD:SA) according to known methods. Briefly, Poly FAD:SA (500 mg, MW 8,600) was melted (60–65° C.) and synthetic TRH (20 mg, Bachem, CA, MW 362) was added to the copolymer to yield a 4% concentration. The melted polymer mixture was cast between two glass plates and allowed to cool to room temperature resulting in a uniform film approximately 0.2 mm thick. A control film with no TRH was produced in a similar fashion. An estimation of TRH release characteristics was determined in vitro by placing a 10% TRH carrier film in 0.1M phosphate buffer pH 7.4 at 37° C. Aliquots were taken periodically to determine the peptide concentration in the buffer using a known method. TRH release from the P(FAD:SA) co-polymer was first order for the first 19–20 hours with no initial TRH burst and attainment of a constant 12% rate of TRH release thereafter from 20 to 70 hours, the last sampled time point (FIG. 1). Having determined its release characteristics, the films were packaged in sealed foil envelopes for storage. At the time of surgery, microstructures (0.4 mm dia.×0.2 mm thick) were punched from films using a specially constructed 22 gauge cannula containing a delivery stylet prior to implantation.

Details of our kindling paradigm have been established previously. Briefly, male Sprague-Dawley rats (300–325 g)(Harlan Industries, Indianapolis) were housed in plastic cages. All animal care and handling was conducted in compliance with the Animal Welfare Act and adhered to principles set forth in the *Guide for the Care and Use of Laboratory Animals*, National Institutes of Health publication 86-23, 1985 edition. Animals were anesthetized with pentobarbital sodium and ketamine (40 mg/Kg, IP.) at the time of surgery. The cannula for delivery microdisks was inserted into the right basolateral amygdalal at coordinates 2.8 mm posterior and 5.0 mm bilateral to the bregma, and 8.5 mm below the surface of the skull. A microdisk containing 90 µg Poly(FAD:SA) 4% TRH (3.6 µg) was inserted into the right basolateral amygdala through the cannula using a stylet. A second group of rats was implanted with a microdisk (2×3.6 µg). A third group of control rats was implanted with a microdisk of 90 µg Poly(FAD:SA) without TRH. After resting 10 min. the cannula was removed. Then, bipolar electrodes where implanted bilaterally into the amygdalae. The stereotaxic coordinates were 7.9 mm ventral to the surface of skull. A reference electrode was inserted in the skull overlying the anterior cortex as previously described. Immediately following and three days after surgery all animals received 50 mg nafcillin (i. m.) to eliminate possible infection. Animals were observed for overt behavioral changes immediately after surgical recovery, and throughout the study.

Five days postoperatively, the afterdischarge (AD) threshold was determined, and a kindling stimulus of 200 $\mu$A was delivered once daily as previously described. The duration of evoked AD and severity of behavioral seizures were recorded following each stimulation session. Behavioral seizures were scored according to a known method, namely, Stage 1, motor arrest, facial automatism, chewing; Stage 2, chewing, and head nodding; Stage 3, forelimb clonus; Stage 4, rearing and forelimb clonus; Stage 5, rearing with forelimb clonus and falling. Animals that had three consecutive Stage 5 seizures where considered fully kindled. After reaching fully kindled status, the animals were maintained in their home cages for an additional 30–40 days until a final stimulus was given to determine if the animals remained kindled. During this period, any animals that lost head caps were removed from the study.

Repeated measures analysis of variance (ANOVA) following the general linear models procedure was used in statistical analysis of the afterdischarge and clonus duration data. Statistical comparisons of the kindling stages data and afterdischarge threshold (ADT) data were made using the Kruskal-Wallis ANOVA by ranks. One-tailed Student's t-tests were used for mean comparisons of kindling permanence at the termination of the study. Data are expressed as MEAN±S.E.M. with (n) the number contributing to the mean. In all cases differences were considered significant at p<0.02.

Results

It was first determined whether the control polyanhydride microdisks or the TRH microdisks had an effect on the afterdischarge threshold (ADT). All threshold currents were in the range required for kindling to occur (40–100 $\mu$A). No statistical differences in stimulating currents were observed among or between right (microdisk) and left (no microdisk) ADT's (data not shown).

As can be seen in Table 1, animals implanted with one or two TRH microdisks required significantly more stimulations (2-fold) to reach each of the five behavioral kindling stages and twice the number of stimulations (8.63±0.924 vs 16.67±1.369; P<0.02) to become fully kindled. This outcome resulted from only one implantation in the seizure focus (stimulated amygdala) and covered a period between 20 to 30 days post implantation. Since no statistically significant difference was observed between implanting one and two microdisks with TRH (Table 1), only results of a single microdisk implant are presented.

TABLE 1

TRH-MICRODISK EFFECT ON KINDLING BEHAVIOR

|  | STAGE 1# | STAGE 2 | STAGE 3 | STAGE 4 | STAGE 5 | KINDLED+ |
|---|---|---|---|---|---|---|
| CONTROL | 1.82 +/− 0.13 | 2.82 +/− 0.13 | 4.09 +/− 0.10 | 5.45 +/− 0.69 | 6.54 +/− 0.93 | 8.63 +/− 0.92 |
| TRH-1 | 4.10 +/− 1.01* | 6.44 +/− 0.81* | 9.22 +/− 1.51* | 11.67 +/− 1.35* | 14.22 +/− 1.30* | 16.67 +/− 1.37* |
| TRH-2 | 3.17 +/− 0.52* | 5.67 +/− 0.88* | 8.00 +/− 0.80* | 9.67 +/− 0.78* | 11.83 +/− 0.59* | 13.83 +/− 0.59* |

Figure 2A:
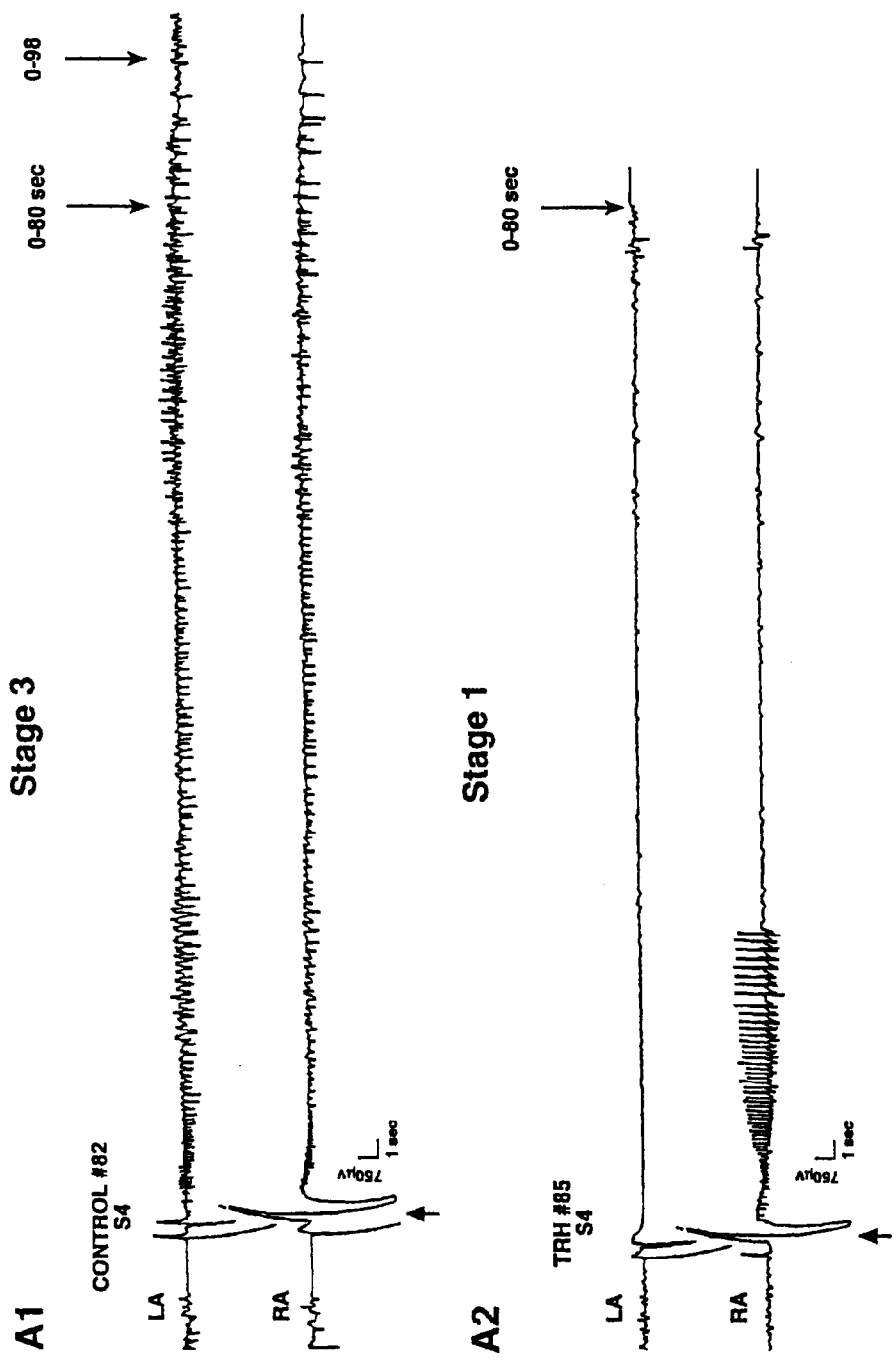
FIG. 2A depicts a representative bilateral EEG recording from amygdalae following the fourth in a sequence of kindling stimulation (S4) wherein the upper two tracings represent a control rat identified as number 82, and the lower two tracings represent a TRH-implanted rat identified as number 85.
Figure 2B:
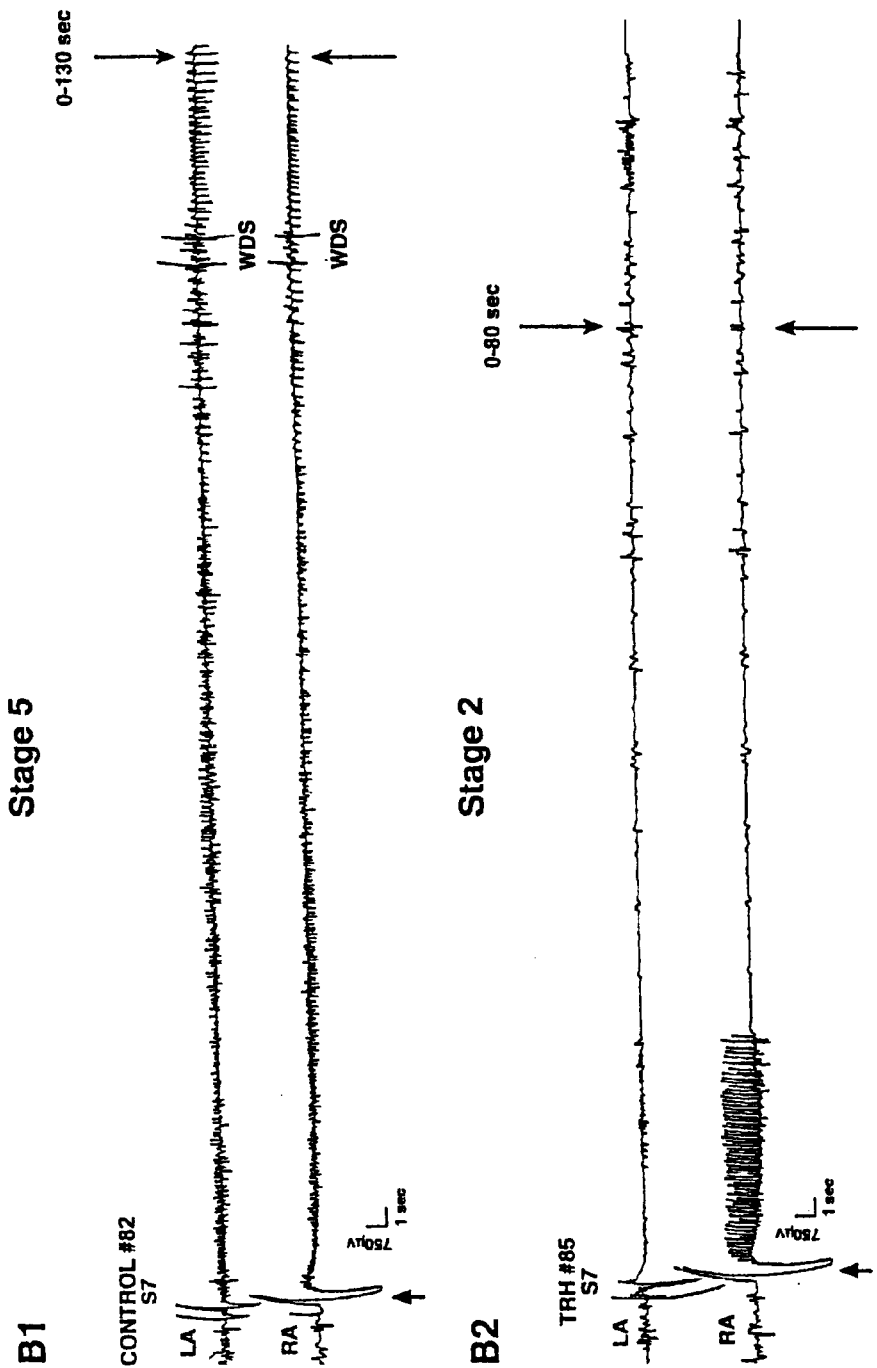
FIG. 2B depicts a representative bilateral EEG recording from the amygdalae after a seventh kindling stimulation, identified as S7, wherein the upper two tracings represent a control rat identified as number 84, and the lower two tracings represent a TRH-implanted rat identified as number 85.

CONTROL = P(FAD:SA) microdisk only (N = 10); TRH-1 = P(FAD:SA) + 3.6 ug TRH (N = 10); TRH-2 = P(FAD:SA) + 7.2 ug TRH (N = 6)
data are expressed as MEAN +/− S.E.M. number of stimulations required to reach Stages 1 through 5
+number of stimulations required to evoke 3 consecutive Stage 5 seizures
*P < 0.02; vs control using Kruskal-Wallis ANOVA by ranks Representative bilateral EEG recordings from the amygdalae after the fourth (S4) and seventh (S7) kindling stimulations are shown in FIGS. 1A & B respectively. Following S4, prolonged (>90 sec.) bilateral AD's were recorded in the control animal (A1), whereas, in the TRH-microdisk subject, (A2) the AD duration in the stimulated amygdala was noticeably shorter while no AD was recorded in the contralateral amygdala was noticeably shorter while no AD was recorded in the contralateral amygdala. Behaviorally, S4 resulted in a Stage 3 response in the control rat, whereas, it produced only a Stage 1 response in the TRH-microdisk animal. An S7 control animal (B1) experienced bilateral AD's greater than 130 sec., whereas in the TRH-implanted subject (B2), the AD duration in the stimulated amygdala was strikingly shorter. Moreover, no AD's were recorded in the contralateral amygdala. Behaviorally, S7 resulted in a Stage 5 generalized seizure in the control animal. This is in marked contrast to only a Stage 2 response in the TRH-microdisk subject (B1 vs B2). The data shown in FIGS. 2A and 2B demonstrate that a single TRH-microdisk significantly shortened the AD duration in both the stimulated (ipsilateral) (P<0.02) and unstimulated (contralateral) (P<0.02) amygdala as well. As seen in FIGS. 2A and 2B, in Panels A and B, the two tracings (A1 and B1) represent control rats (#82, #84) respectively, while, the lower two tracings (A2 & B2) represent TRH-microdisk rat #85. A 200 $\mu$A stimulation (↑) was given to the right amygdala (RA) of each animal, whereas, the (contralateral) left amygdala (LA) was unstimulated. S4 (Panel A) resulted in a prolonged AD duration (98 sec. ↓) from both the RA and LA of the control animal (tracing A1). In marked contrast, tracing A2 depicts a short series of afterdischarges (AD's) (24 sec.) from the stimulated RA and an absence of stimulus transfer to the contralateral LA of the THR-microdisk animal. Behaviorally, S4 resulted in a Stage 3 response in the control rat (A1), whereas, only a Stage 1 response was observed in the THR microdisk animal (A2). S7 (Panel B), resulted in prolonged AD durations (>130 sec. ↓) from both the RA and LA of the control animal (tracing B1). In marked contrast tracing B2 depicts a much shorter series of AD's (28 sec.) from the stimulated RA and an absence of transfer to the contralateral LA of the TRH-microdisk animal. Behaviorally, S7 resulted in a Stage 5 generalized seizure in the control rat (B1), whereas, only a Stage 2 response was observed in the TRH microdisk animal (B2). WDS indicates Wet Dog Shakes.

Figure 4:
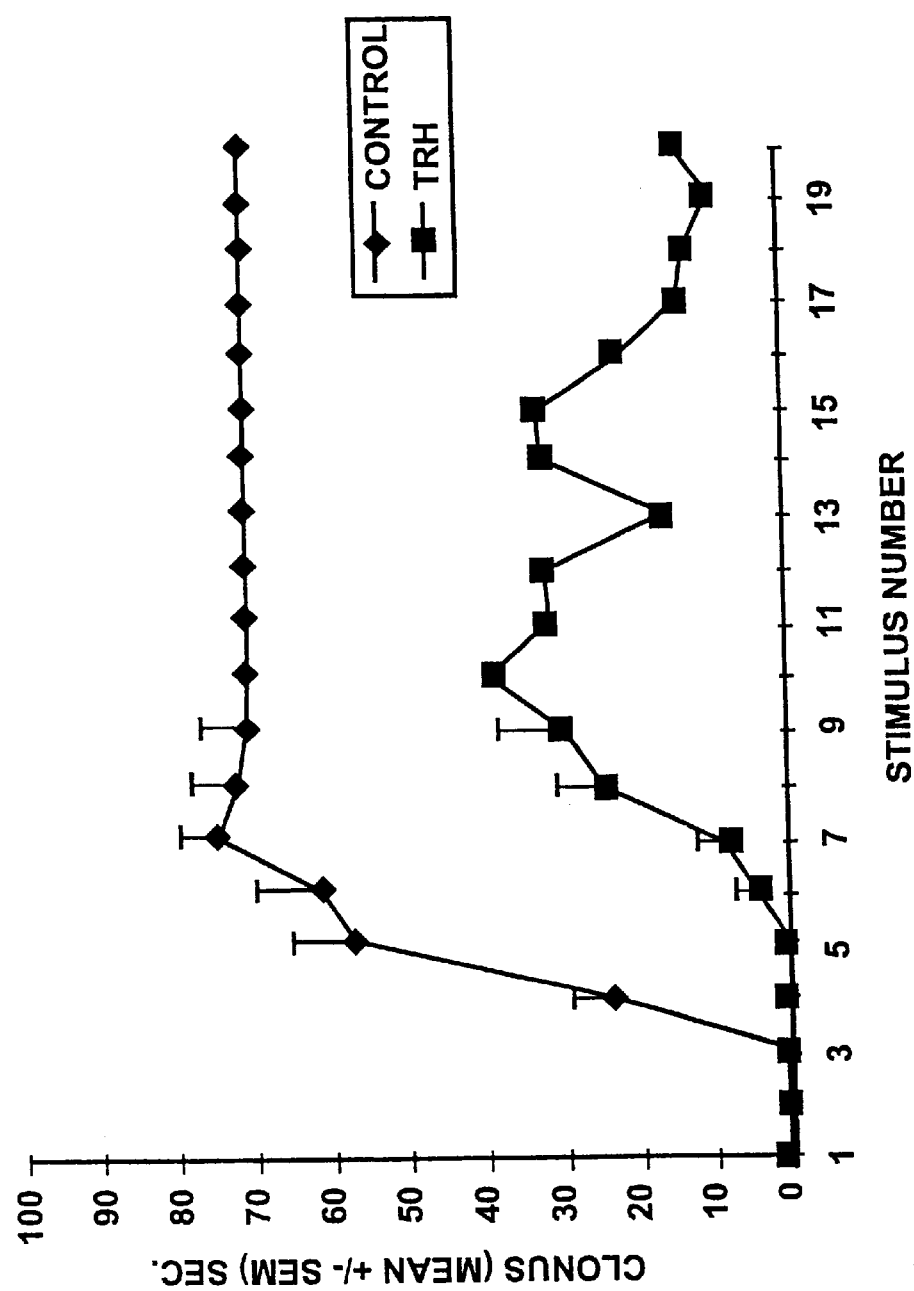
FIG. 4 is a graph of clonus as a function of stimulus number, which compares a control microstructure with a microstructure containing TRH.
Figure 5:
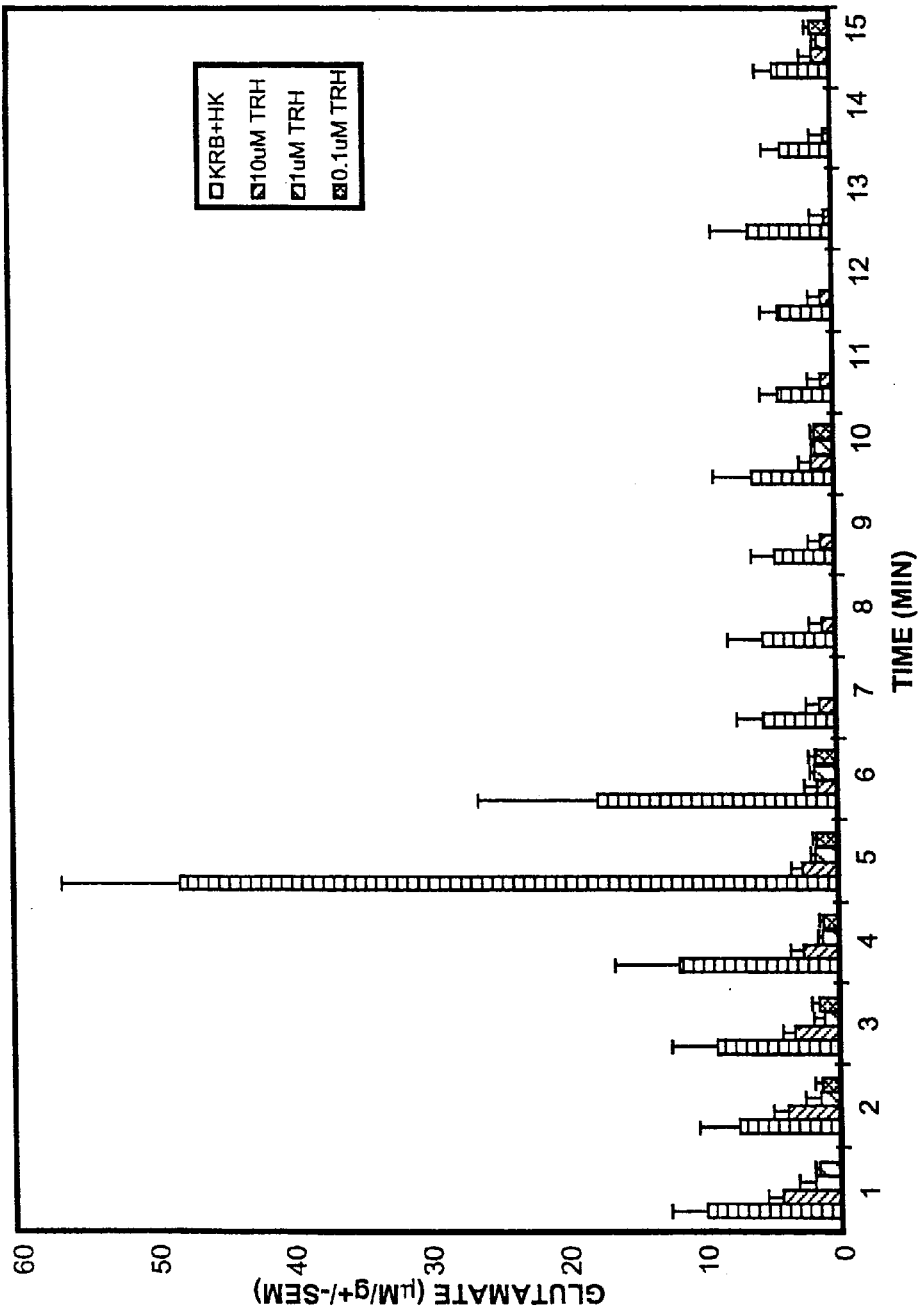
FIG. 5 is a graph of glutamate release as a function of time following high potassium stimulation (KRB+HK), which shows the inhibiting effect of TRH at different concentrations on glutamate release from rat hippocampal slices.

The effects of a single microdisk on clonus duration (muscle shakes) are shown in FIG. 4. As seen in FIG. 4, clonus was significantly shorter (P<0.02) in the TRH-microdisk implanted group (■) than in the control group (◆). Control=microdisk only (n=10); TRH-microdisk=3.6 µg TRH (n=10). Statistical analysis was performed using repeated measures ANOVA. Control symbols (◆) beyond the 9th stimulus are representative average clonus values and are included as reference points. Standard error bars have not been included in mean TRH data points (■) beyond the 9th stimulus as the number of animals contributing to the mean decreases as the subjects become fully kindled. Here it can be seen that the TRH-implant significantly ($P<0.02$) suppressed clonus duration during kindling development and after fully kindled generalized seizures. Between the time the animals were implanted with microdisks and kindling permanence testing (termination of the study), no apparent behavioral changes were noted. When the last seizure was evoked, between 50 and 60 days after initial ADT testing, all remaining animals had Stage 5 generalized seizures. Surprisingly, in the TRH-implanted groups a significant reduction in clonus duration ($53.90\pm3.27$ vs $40.09\pm4.14$; $p<0.02$) remained, as well as a tendency toward a reduced AD duration both ipsilaterally ($P=0.13$) and contralaterally ($P=0.27$)(Table 2). Histologically, other than local electrode scarring, no cytotoxicity or microdisk material was apparent at the implant sites in the amygdala of control or TRH implanted groups (data not shown).

fully kindled. The sustained release preparation substantially enhanced the antiepileptogenic and anticonvulsant efficacy of TRH over previously observed pharmacological studies. In terms of suppressive effects on both kindling evolution and seizure severity, the single TRH-implant was comparable to existing repeatedly administered clinically relevant anticonvulsant drugs. These results are striking and provide strong evidence for an antiepileptogenic/anticonvulsant function of TRH in the temporal lobe.

As noted above, the amygdala is a key site of kindled epileptogenesis and has widespread interconnections with cortical and subcortical areas. Therefore, it seems reasonable to conclude that site-specific sustained delivery of TRH is effective in substantially decreasing the level of excitability of amygdala efferents and it retards the rate of seizure spread (or generalization) throughout the brain for a prolonged period.

Figure 3A:
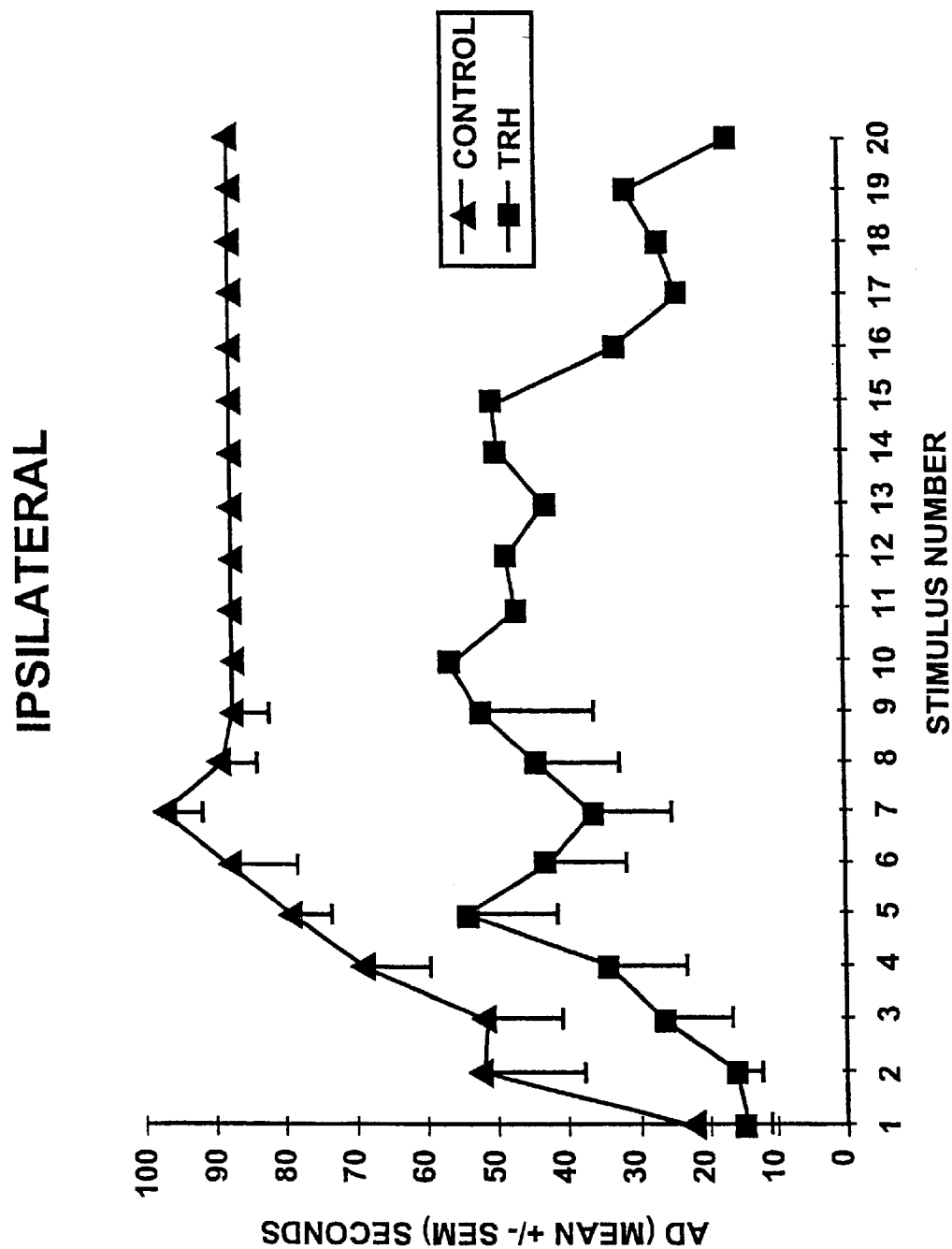
FIG. 3A is a graph illustrating afterdischarge duration (AD) in an ipsilateral amygdala as a function of stimulus number, which compares a control microstructure with a microstructure containing TRH.
Figure 3B:
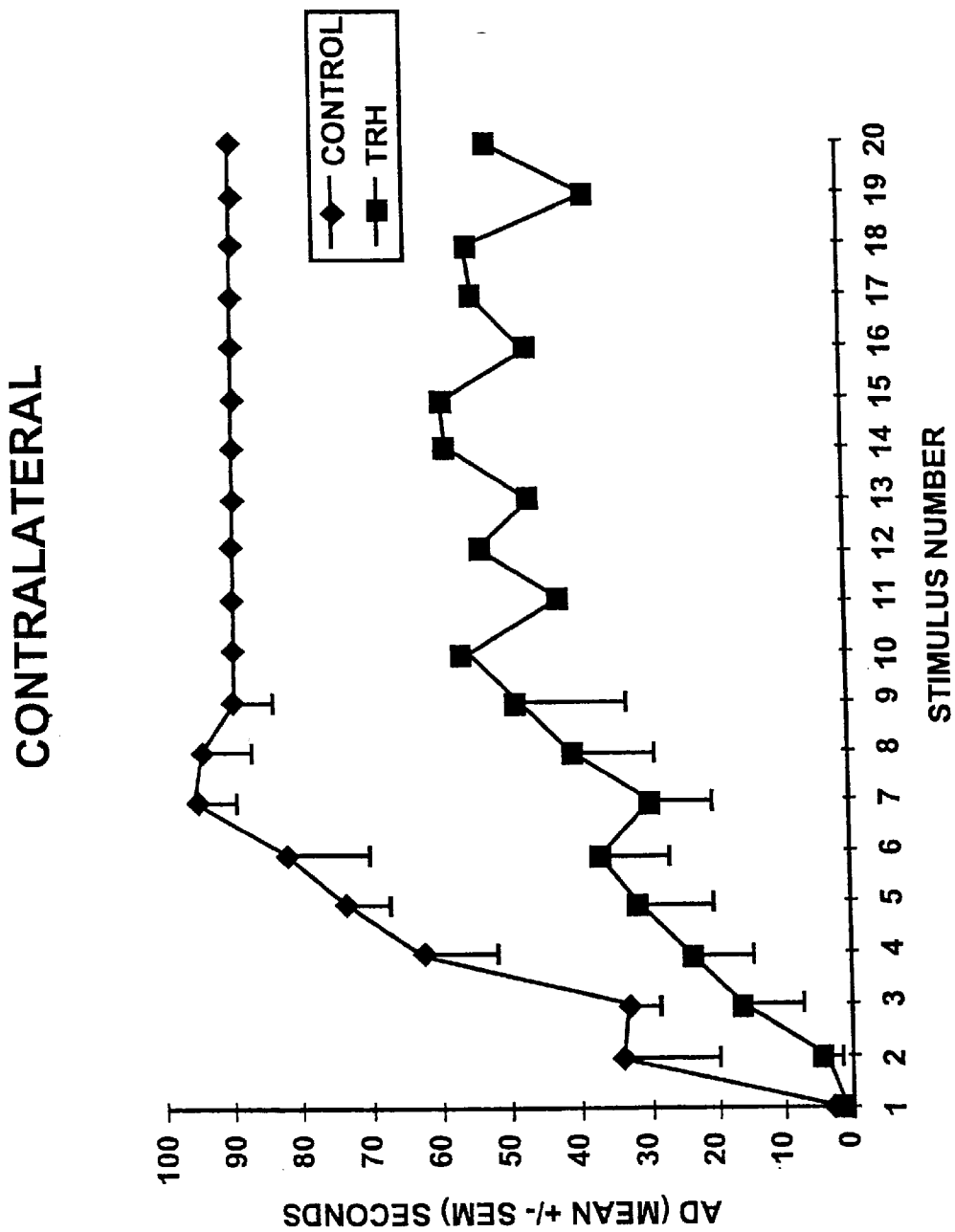
FIG. 3B is a graph illustrating afterdischarge duration (AD) in the contralateral amygdala as a function of stimulus number, which compares a control microstructure with a microstructure containing TRH.

The TRH implant had a marked effect on both ipsilateral and contralateral AD's even when the animals became fully kindled as seen in FIGS. 3A and 3B. It has been suggested that anticonvulsant drugs that have the most marked impact on AD duration also tend to more efficaciously suppress behavioral symptoms. The TRH-microdisk implant had a marked effect on clonus duration; completely suppressing it

TABLE 2

PROLONGED EFFECT OF TRH-MICRODISK ON SEIZURE SEVERITY

|  | DAYS after ADT[+] | AD DURATION# | | CLONUS DURATION# |
|---|---|---|---|---|
|  |  | IPSILATERAL | CONTRALATERAL |  |
| TRH | 48.64 +/− 4.98 | 71.91 +/− 10.02 | 82.80 +/− 10.19 | 40.09 +/− 4.14* |
| CONTROL | 56.60 +/− 4.17 | 85.90 +/− 7.99 | 91.20 +/− 9.60 | 53.90 +/− 3.27 |

CONTROL = P(FAD:SA) microdisk only (N = 10); TRH = P(FAD:SA) +3.6 ug TRH (N = 6) and 7.2 ug TRH (N = 5)
all animals had a Stage 5 generalized seizure; data are expressed as (MEAN +/− S.E.M.) in seconds
[+]afterdischarge threshold testing
*$P < 0.02$ vs control (one tailed t-test)

Discussion

The data clearly demonstrate that a single biodegradable polymeric-TRH implant is capable of suppressing the development of kindling expressed as the number of stimulations required to reach each behavioral stage, and the number needed to reach full kindling (Table 1). The TRH implant delayed kindling transfer to the contralateral amygdala as seen in FIGS. 2A and 2B, and significantly shortened the AD duration in both the ipsilateral (stimulated) and contralateral amygdala during kindling. In fact, the mean AD in the TRH-microdisk group was approximately 40 sec. less than the control, during and even when the animal became fully kindled, as seen in FIGS. 3A and 3B, in the ipsilateral (stimulated) amygdala, stimulus evoked AD's in TRH-microdisk group (■) were significantly shorter ($P<0.02$) than in the control group (▲) (upper graph). In the contralateral (unstimulated) amygdala, the TRH group (■) had significantly shorter ($P<0.02$) AD's than its corresponding control group (◆) (lower graph). Control=microdisk only (n=10); THR-microdisk=3.6 µg TRH (n=10). Statistical analysis was performed using repeated measures ANOVA. Control symbols (▲ ◆) beyond the 9th stimulus are representative average AD values at the completion of the study (Table 2) and are included as reference points. Standard error bars have not been included in mean TRH data points (■) beyond the 9th stimulus as the number of animals contributing to the mean decreases as the subjects become at the 4th and 5th stimulations and reducing it 12- and 8-fold by the 6th and 7th stimulations respectively. Beyond the 7th stimulation, and at the time the animals became fully kindled (16.67 stimulations), clonus was still substantially reduced as seen in FIG. 4. Moreover, this effect on clonus persisted until the termination of the study even though at that time the AD's were not significantly different from controls (Table 2). This prolonged effect on myoclonus was surprising since evidence for the implants remaining was not apparent. This finding argues in favor of a possible long-term effect of TRH on seizure severity. Obviously, a more quantitative assessment of TRH levels at the implant site is required before such a hypothesis could be supported.

Implanted microdisks (with or without TRH) had no effect on the ADT prior to kindling, and no apparent change in normal animal behavior was evident throughout the study. This suggests that polymeric-TRH may be implanted into a known or potential seizure focus without affecting ongoing activity.

Our results indicate that TRH-ISMP may provide an alternative treatment, one that could significantly impede or possibly prevent epileptogenesis where more conventional therapies have not been successful. Since TRH is known to potentiate the anticonvulsant potency of phenobarbital, and also to be essential in maintenance of the anticonvulsant efficacy of carbamazepine, perhaps a combination of TRH-ISMP and conventional drug therapy could potentiate a drug's anticonvulsant efficacy while reducing its side effects in patients with intractable epilepsy.

EXAMPLE 2

Figure 6:
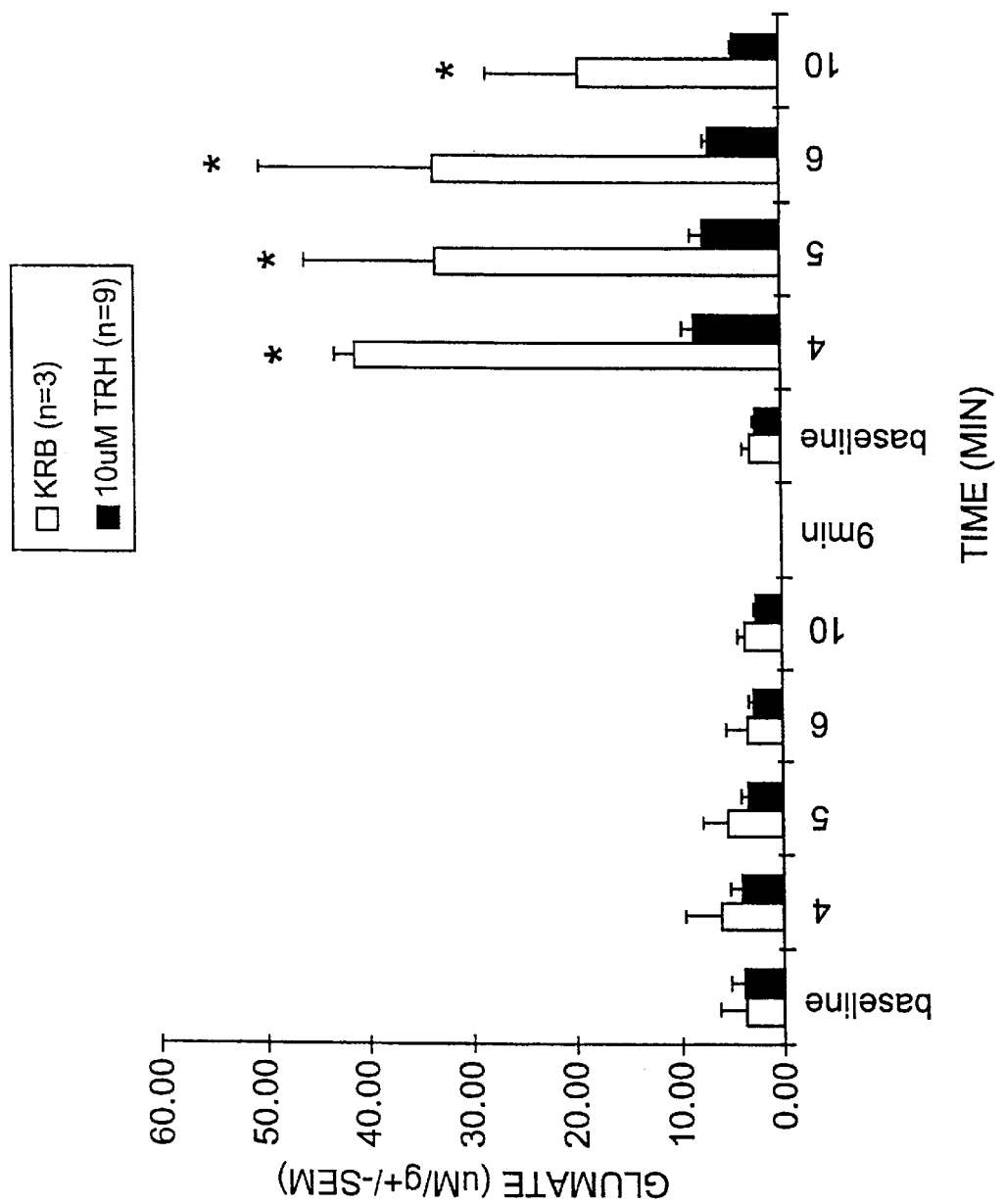
FIG. 6 is a graph illustrating prolonged inhibitory effect of TRH on potassium stimulated glutamate release.

TRH INHIBITION OF [K$^+$]-STIMULATED GLUTAMATE RELEASE FROM HIPPOCAMPAL SLICES IN VITRO. Enhanced excitatory amino acid release is suspected in pathways associated with seizures and excitotoxicity. In this regard, superfused hippocampal slices were used to investigate the hypothesis that TRH could inhibit glutamate release in vitro. Rat hippocampi were removed and sliced transversely (500 µm) under low magnification. Slices were weighed, washed in cold saline, transferred to individual tissue chambers floated in a 37° C. water bath and were equilibrated in oxygenated (95% $O_2$/5% $CO_2$), (37° C.) Kreb's buffer (KRB) for 120 min. (0.5 ml/min.). Slice chambers were then superfused 10 min. with KRB (control), or KRB containing 10 µM, 1 µM, or 0.1 µM TRH respectively, prior to 5 min. stimulation with modified KRB (50 mM [K$^+$]±TRH). Fractions (1 min.) were collected during the 5 min. stimulation and for an additional 10 min. (0.5 ml/min.) thereafter, and analyzed for glutamate by HPLC. Data were expressed as µM/g/fraction±S.E.M. All three TRH doses significantly ($p<0.001$), but not dose-dependently, inhibited peak 50 mM [K$^+$]-stimulated glutamate release (48.05±8.59 vs 2.35±0.50, 1.54±0.33, 1.38±0.28) respectively and glutamate remained below control ($p<0.05$) at 10 min. post stimulation (4.37±1.29 vs 1.35±0.48, 1.11±0.26, 1.54±0.43) respectively. As seen in FIG. 6, perfusion (5 min.) with KRB±10 µM TRH significantly ($p<0.05$) blocked glutamate release by 50 mM [K$^+$]-stimulation given 15 min. later. These results are the first to show a potent and prolonged inhibitory effect of TRH on glutamate release in vitro. It is suggested that endogenous TRH is anticonvulsant/neuroprotective and in part, may function to modulate glutamate release in certain neurological disorders such as epilepsy.

While the preferred embodiments of the invention have been disclosed, it should be appreciated that the invention is susceptible to modification without departing from the spirit of the invention or the scope of the subjoined claims.

What is claimed is:

1. A method for selectively increasing release of a predetermined endogenous compound comprising the steps of:
    selecting an in situ locus in the central nervous system which includes agonist receptors and heterologous receptors that are coupled to common G-proteins; and
    stereotaxically delivering to the in situ locus at least one biodegradable, non-spherical polymeric microstructure comprising an agonist and a pharmaceutically acceptable carrier, wherein the microstructure has a size and shape sufficient to prevent dispersion from the locus, and wherein the microstructure provides sustained release of the agonist via surface erosion to effectively upregulate G-proteins common to the agonist receptor and the heterologous receptor to potentiate the heterologous receptor in order to increase release of the endogenous compounds released by the heterologous receptor.

2. A method as defined in claim 1 wherein the delivering step includes restricting the microstructure to a diameter ranging from approximately 0.3 mm to approximately 5 mm.

3. A method as defined in claim 1 wherein the delivering step includes restricting the microstructure to a thickness ranging from approximately 0.1 mm to approximately 5 mm.

4. A method as defined in claim 1 wherein the endogenous compound is selected from the group consisting of neurotransmitters, neuropeptides and hormones.

5. A method as defined in claim 4 wherein the endogenous compound includes a neurotransmitter selected from the group consisting of GABA$_B$, acetylcholine and dopamine.

6. A method as defined in claim 5 wherein the endogenous compound includes a neuropeptide selected from the group consisting of TRH, NPY, CCK and NT.

7. A method as defined in claim 4 wherein the endogenous compound includes a hormone selected from the group consisting of glucagon and melatonin.

8. A method as defined in claim 1 wherein the carrier includes a polymer.

9. A method as defined in claim 8 wherein the polymer comprises a polyanhydride.

10. A method as defined in claim 8 wherein the polymer is selected from polymeric oleic acid dimers and polymeric sebacic acid monomers, or combinations thereof.

11. A surface-eroding polymeric composition for stereotaxic administration at an in situ locus in the central nervous system to increase release of an endogenous compound comprising:
    an agonist; and
    a pharmaceutically acceptable carrier comprising a polyanhydride, wherein the pharmaceutically acceptable carrier provides sustained release of the agonist via surface erosion at a rate effective to upregulate a G-protein coupled to the agonist receptor which, in turn, potentiates a heterologous receptor coupled to the G-protein to increase release of the endogenous compound at the locus, wherein the composition is shaped in the form of a non-spherical microstructure having a size and shape sufficient to prevent dispersion from the in situ locus in the central nervous system where it is stereotaxically administered.

12. A composition as defined in claim 11 wherein the carrier is selected from the group consisting of oleic acid dimer polymers, sebacic acid monomer polymers, and combinations thereof.

13. The method of claim 1 wherein release of more than one endogenous compound is increased.

14. The composition of claim 11, wherein the microstructure undergoes surface erosion at a rate less than 3.5 π(dl/dt), where l is a characteristic size of the microstructure and (dl/dt) is the time rate of change of l.

* * * * *